(12) United States Patent
Mertelmeier et al.

(10) Patent No.: US 7,020,319 B2
(45) Date of Patent: Mar. 28, 2006

(54) METHOD AND APPARATUS FOR GENERATING THREE-DIMENSIONAL, MULTIPLY RESOLVED VOLUME IMAGES OF AN EXAMINATION SUBJECT

(75) Inventors: Thomas Mertelmeier, Erlangen (DE); Norbert Strobel, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 573 days.

(21) Appl. No.: 10/269,686

(22) Filed: Oct. 11, 2002

(65) Prior Publication Data

US 2003/0081821 A1    May 1, 2003

(30) Foreign Application Priority Data

Oct. 11, 2001 (DE) ................ 101 50 428

(51) Int. Cl.
*G06K 9/00* (2006.01)

(52) U.S. Cl. .................. 382/132; 378/4; 378/163; 378/901

(58) Field of Classification Search ........ 382/128–134; 378/4, 17, 98.4, 98.6, 98.9, 101, 163, 901; 128/916, 920; 600/444; 250/363.03, 363.04, 250/369, 371, 375, 559.19, 559.21, 577
See application file for complete search history.

(56) References Cited

U.S. PATENT DOCUMENTS

| | | | | |
|---|---|---|---|---|
| 5,433,202 A | * | 7/1995 | Mitchell et al. | 600/444 |
| 5,489,782 A | * | 2/1996 | Wernikoff | 250/369 |
| 6,298,110 B1 | * | 10/2001 | Ning | 378/4 |
| 6,438,198 B1 | * | 8/2002 | Kohler | 378/15 |

FOREIGN PATENT DOCUMENTS

| | | |
|---|---|---|
| DE | OS 195 24 858 | 1/1997 |
| DE | OS 199 35 093 | 2/2001 |

* cited by examiner

*Primary Examiner*—Jingge Wu
*Assistant Examiner*—Abolfazl Tabatabai
(74) *Attorney, Agent, or Firm*—Schiff Hardin LLP

(57) ABSTRACT

In a method and examination apparatus for generating three-dimensional, multiply resolved volume images of an examination subject on the basis of two-dimensional projection images that can be registered with the apparatus, as radiation images obtained with a radiation source and a radiation receiver in an exposure procedure of the examination subject, a set of two-dimensional projection images is registered, one part of the set being registered with low resolution and one part of the set being registered with high resolution, transforming the high-resolution projection images are transformed so as to have the same scale, the same sampling rate and the same resolution as the low-resolution projection images (downscaling), and a three-dimensional volume image with low resolution is generated on the basis of the low-resolution projection images as well as the transformed projection images and a high-resolution volume image is generated on the basis of the high-resolution projection images.

17 Claims, 4 Drawing Sheets

METHOD AND APPARATUS FOR GENERATING THREE-DIMENSIONAL, MULTIPLY RESOLVED VOLUME IMAGES OF AN EXAMINATION SUBJECT

BACKGROUND OF THE INVENTION

1. Field of the Invention

The present invention is directed to a method for generating three-dimensional, multiply resolved volume images of an examination subject on the basis of two-dimensional projection images that can be registered (acquired) with an apparatus for producing radiation images, with a radiation source and a radiation receiver in an exposure procedure of the examination subject.

2. Description of the Prior Art

In methods of this type which are often utilized for generating and displaying images that can be medically interpreted, a number of two-dimensional projections are registered in order to obtain a good contrast resolution. A high number of projections, however, significantly increases the quantity of projection data, and it is expected that far more projections than is currently conventional, namely several hundred, will be registered in future applications. Additionally, the demands made on the transmission bandwidth, the processing and the storage of such data are also increasing explosively. One solution to this problem is to reduce the number of detector elements of the radiation detector in the underlying, two-dimensional detector matrix. This can be achieved by a technique referred to as "pixel binning", whereby neighboring detector elements or pixels are combined and, for example, a signal average to be further-processed for this pixel cluster region is generated from the individual signals. Since, however, the detector area does not change, pixel binning results in a lower spatial resolution since a larger, effective pixel size is employed for covering the same detector region as was covered by multiple pixels. Disadvantageously, larger detector pixels or binned regions not only lower the spatial resolution at the detector but also the spatial resolution in the appertaining volume dataset. In applications wherein a high spatial resolution and a good recognizability of low-contrast subjects are required, a lowering of the spatial resolution is not desirable.

German OS 199 35 093 discloses a CT apparatus with a multi-line detector system wherein different columns of the detector system are connectable to a different number of electronics elements for the readout of the signals generated in the detector elements. Further, German OS 199 56 585 discloses a computed tomography method wherein an improved compromise between transmission bandwidth and image quality is achieved by combining the signals of at least two neighboring detector elements are combined into a measured value and a cyclic variation of the combination ensues from radiation source position-to-radiation source position. Further, German OS 195 24 858 discloses an X-ray generating system that is fashioned such that different image resolutions can be achieved in an economical way, an a-Si:H detector being provided for this purpose that is constructed of a number of sub-detectors lying in a plane, with respectively different resolutions.

SUMMARY OF THE INVENTION

An object of the present invention is to provide a method and examination apparatus which enable the generation of differently resolved volume images from one projection dataset of individual 2D projections.

This object is achieved in a method of the type initially described including, in a first embodiment, the steps of registering a set of two-dimensional projection images, one part of the set being registered with low resolution and one part of the set being registered with high resolution, transforming the high-resolution projection images such that they comprise the same scale, the same sampling rate and the same resolution as the low-resolution projection images (downscaling), and generating a three-dimensional volume image with low resolution on the basis of the low-resolution projection images as well as the transformed projection images and generating a high-resolution volume image on the basis of the high-resolution projection images.

The basis of the invention to calculate two volume images from two-dimensional projection images that were registered during a single exposure event of the examination subject, i.e. during a single revolution of the radiation source and the radiation receiver around the examination subject with different spatial resolutions. In accordance with the invention two different image groups are registered within a set of projection images. One group is projection images with low resolution, whereas the other group is projection images with high resolution. To this end, the detector resolution can be varied in a pre-defined sequence, for example switched in alternation between a high and a low resolution. Subsequently, the high-resolution projection images are first filtered with a low-pass filter during the course of a downscaling and are subsequently adapted in scale, or the sampling rate to the low-resolution projection images in a down-sampling, i.e. all projection images are subsequently in the same scale regardless of their resolution. The transformed high-resolution projection images thus have the same number of pixels as the low-resolution projection images. Finally, the generation of two three-dimensional volume images ensues from the two different sets of projection images, preferably by filtered back-projection, namely a high-resolution image and a low-resolution volume image. The same filters can be employed in of the filtered back-projection for generating both volume images as a result of the previously undertaken downscaling step.

The reconstruction of a volume image becomes all the more diagnostically relevant and precise as more projections are available for the reconstruction, e. g. using a filtered back-projection algorithm. For generating the volume image with low resolution, consequently, it is expedient when the high-resolution projection images are also employed, the resolution thereof having been reduced for this purpose. The high-resolution volume images thus are post-processed such that they have the same resolution after the processing as the low-resolution projection images, so that they can be integrated into the set of low-resolution projection images. The spatial resolution of the high-resolution projection images is thus computationally reduced by the filtering with a low-pass filter and the subsequent down-sampling. After this "downscaling", the originally high-resolution projection images that have been reduced in resolution as well as the originally low-resolution projection images are available for the reconstruction of a further volume image since all projection images then have a uniform resolution as well as a uniform scale and a uniform sampling rate. A volume that offers a better contrast resolution than would be the case given employment of only the originally lower number of low-resolution images can now be calculated on the basis of the increased number of processable projection images and their lower detector resolution.

A maximum number of projection images is not absolutely necessary for the reconstruction of a volume image with adequately high resolution for the diagnosis of subjects; on the contrary, a volume image can be reconstructed using a reduced number of images. Given an adequately high image registration rate per scan, an adequate number of high-resolution projection images are available—despite the resolution variation—so that a diagnostically relevant volume image with high spatial resolution can be reconstructed.

Inventively, thus, two differently resolved volume images are obtained, the volume image with low resolution exhibiting a good contrast resolution, and the high-resolution volume image exhibiting a high spatial or topical resolution. It should be noted, however, that it is not absolutely necessary to employ the same filters or operators for the reconstruction and for the presentation of the two volume datasets. This offers an additional degree of freedom to the effect of emphasizing different properties of the various volume datasets dependent on the demands, i.e., for example, to work differently in view of the contrast resolution or spatial resolution to be achieved or the like.

The two volume images then can be output in different ways to the user, for example, the physician. There is the possibility of outputting the two images individually or simultaneously separately at a monitor; an overlaid presentation of the two volume images is also possible.

It is expedient when the generation of the low-resolution projection images ensues by interconnecting a number of pixels of the radiation detector that lie side-by-side (pixel binning). Such radiation detectors that enable a fast switching of the detector resolution are known; such as CMOS detectors.

The low-resolution and high-resolution projection images are inventively registered in a pre-defined, alternating sequence. It is expedient when, given exposure of N projection images, every nth projection image is registered with high resolution. For example, every tenth projection image can be registered with high resolution. Of course, it is also possible to generate projection image datasets that are of the same size but differently resolved, with the resolution being varied in alternation in every projection image exposure.

As described, the generation of volume images can ensue by means of filtered back-projection, but this is not compulsory. When the filtered back-projection is employed, it is expedient when a filter that promotes the contrast resolution is employed for generating the low-resolution volume image. Further, a filter that promotes the spatial resolution can be employed for generating the high-resolution volume image.

The advantages of this inventive method are that two differently spatially resolved volume images can be obtained with only one scan. Using the same exposure equipment, i.e. the same hardware, further, clearly more views and projections can be registered, on the basis of the mixed data registration with respect to the resolution and the later processing, than was previously the case given a full resolution data registration. Ultimately, the user also obtains significantly more information from a single scan, namely two separate, diagnostically relevant volume images.

In a method of the type initially described, a radiation receiver with a high-resolution reception region and a low-resolution reception region is additionally employed, the aforementioned object also is achieved in a second embodiment including the steps of registering a set of two-dimensional projection images that have high-resolution in one portion and low-resolution in another portion with a radiation detector, with the lowly resolved portion being generated by interconnection of neighboring detector elements, interpolating the low-resolution portion of each projection image for adapting the sampling rate thereof such that the sampling rate of the low-resolution portion is equal to the sampling rate of the high-resolution portion, and implementing a filtered back-projection of the projection images with a uniform sampling rate for generating a volume image having a volume portion with high resolution and a volume portion with low resolution.

This embodiment of the invention is also based on calculating a three-dimensional volume image proceeding from volume images that were registered in a single revolution of the image exposure equipment around the examination subject, this volume image having different resolution by portions, i.e. it is composed of a portion with low spatial resolution and high contrast resolution and a of portion with high spatial resolution and lower contrast resolution in exchange. Here, too, projection images are registered with portions of high and low spatial resolution. This development of the invention utilizes a detector that, first, differs region-by-region in resolution or that can be correspondingly switched. Such detectors, for example, are known as "Fovea detectors". Each acquired projection image is in turn composed of a high-resolution portion and of a low-resolution portion. These projection images are processed after registration, or the low-resolution portion is interpolated, such that the sampling rate is the same over the entire, processed projection image, i.e. in the low-resolution portion as well as in the high-resolution portion. This is required in order to be able to subsequently employ uniform filters within the filtered back-projection for generating the volume image, or in order to be able to undertake a filtered back-projection at all. In the final analysis, a volume image is obtained that contains two different volume regions or portions, namely a portion of low resolution and a portion of high resolution. Here, too, the user or physician receives different information from the differently resolved image portion in the ultimately reconstructed volume image from the registration of only one projection dataset, i.e. the implementation of one scan. Here, too, the volume image reconstruction ensues by means of filtered back-projection or, more precisely, in a conical beam tomography method that reconstructs projection images with a uniform sampling rate to form a volume image.

A radiation detector that inherently has high spatial resolution can be employed as the radiation detector, and the generation of the portion of low spatial resolution in the projection image is achieved by interconnecting a number of pixels lying side-by-side, i.e. by pixel binning in this case as well. In addition to a radiation detector that is permanently prescribed or defined in view of the regions with different spatial resolution, a radiation detector can be employed wherein a variable high-resolution region can be set, i.e. the image region with high spatial resolution can vary from projection image-to-projection image. This also ensues by means of very fast pixel binning.

In the second embodiment of the inventive method, the following steps can ensue the interpolation. The example below assumes that there are two regions with respective resolutions differing from one another by a factor of two.

The high-resolution region of each projection image is processed using a separable two-dimensional wavelet transformation employing a low-pass filter and a high-pass filter, so that a band matrix having four sub-bands is obtained, one of which contains only the low-pass part of the projection image in the form of approximation coefficients and the other three sub-bands containing various high-pass parts of the projection image in the form of detail coefficients. The sub-band containing the approximation coefficients is integrated instead of the high-resolution region of the original projection image for forming an integration image with lower spatial resolution. The integration image is employed as a low-pass sub-band of a second band matrix.

The three other sub-bands of the imaginary band matrix are filled with the detail coefficients of the already existing sub-bands at coefficient-related band positions and with filler coefficients (for example, having the value zero) at other band positions.

The filled band matrix is subjected to an inverse wavelet transformation.

Subsequently, all projection images processed in this way are subjected to the filtered back-projection reconstruction algorithm. The utilization of a wavelet transformation thus indicates a quasi-fixed function diagram as to the mathematical description of the filtering or of the entire interpolation. The wavelet method allows a consistent interpolation of the low-resolution projection image region.

The aforementioned steps within the interpolation can be in accordance with the invention repeated with respect to a projection image until the sampling rate or the scale of the low-resolution corresponds to that of the high-resolution region.

In addition to the inventive method, the above object also is achieved in an apparatus for the exposure of radiation images that is fashioned for the implementation of one or both embodiments of the inventive method.

DESCRIPTION OF THE PREFERRED EMBODIMENTS

Figure 1:
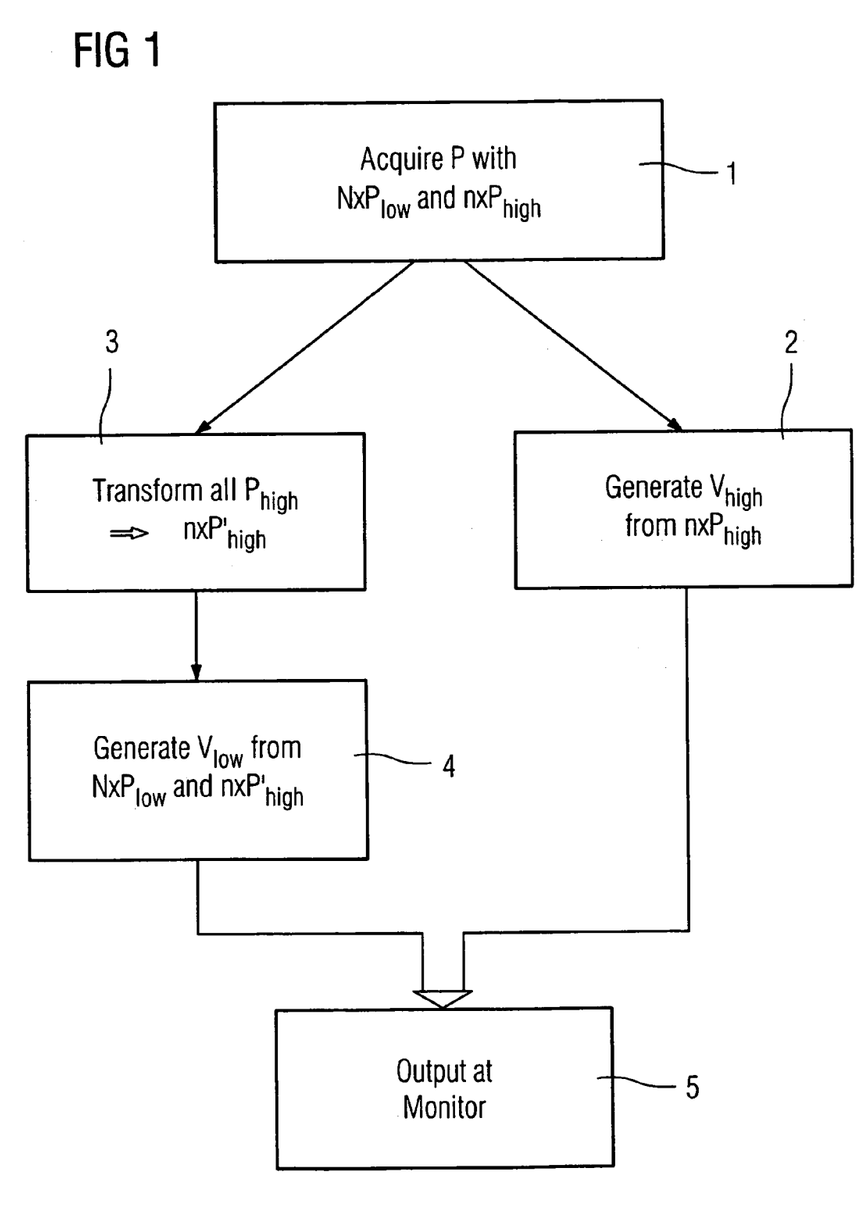
FIG. 1 is a functional diagram of the inventive method for generating two separate volume images from differently resolved projection image sets.

In the form of a function flowchart, FIG. 1 shows the basic steps for generating two separate volume images with different resolution. In step 1, a complete projection image dataset P is first registered in a scan, this dataset P being composed of N low-resolution projection images, referred to below as $P_{low}$, and n high-resolution projection images, referred to below as $P_{high}$. Subsequently, the generation of a high-resolution volume image $V_{high}$ ensues in step 2 from the n high-resolution projection images $P_{high}$.

In step 3, all high-resolution projection images $P_{high}$ are transformed such that their scale and sampling rate correspond to the scale and sampling rate of the low-resolution images. A downscaling with a low-pass filter and a downsampling, i.e. an ordered discarding of pixels, thus occur. A number n of transformed, high-resolution projection images $P'_{high}$ are obtained. In step 4, a low-resolution volume image $V_{low}$ is then generated from the totality of N low-resolution projection images $P_{low}$ and the n, now low-resolution, previously high-resolution projection images $P'_{high}$. In step 5, these two volume images are then presented at a monitor, in individual presentation, above or next to one another, or in an overlaid form.

It should be noted that step 3 can be omitted, and the generation of the low-resolution volume image $V_{low}$ can ensue exclusively from the N low-resolution projection images $P_{low}$.

The generation of the respective volume images expediently ensues by means of filtered back-projection. Different filters can be employed for this dependent on what demands are made of the respective volume image. It is expedient to employ a filter that promotes the contrast resolution for generating the low-resolution volume image in order to be also able to recognize slight contrast filter differences of even small subjects in the volume image. A filter with high topical or spatial resolution is expediently utilized for generating the high-resolution volume image $V_{high}$.

Figure 2:
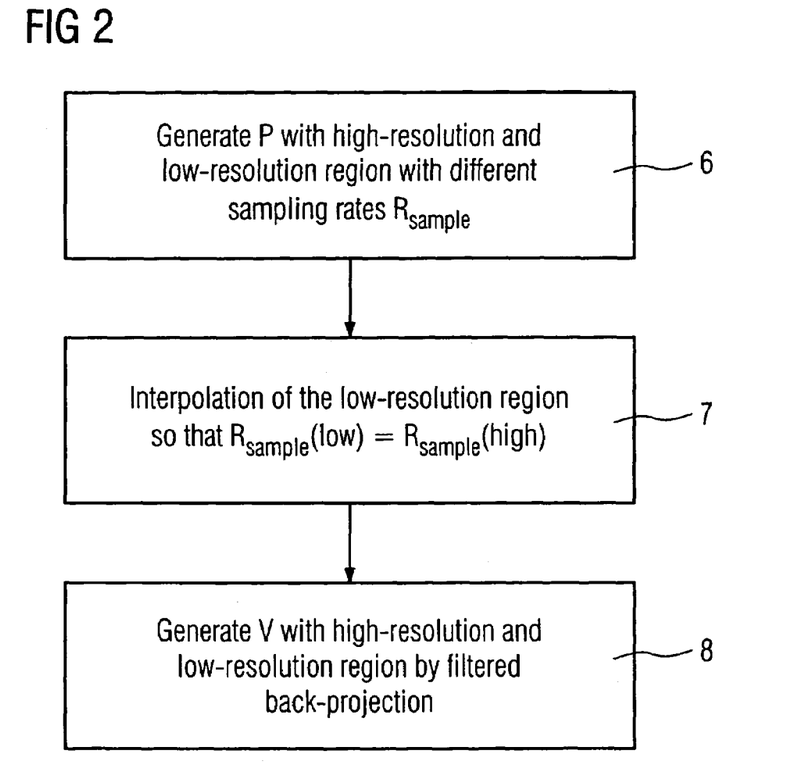
FIG. 2 is a functional diagram of the inventive method for generating a volume image with differently resolved volume regions.

FIG. 2 is a flowchart for illustrating the inventive method wherein a volume image resolved differently by portions is generated. In step 6, a set of projection images P is registered with a high-resolution portion and a low-resolution portion, the two portions having different sampling rates $R_{sample}$. An interpolation of the low-resolution portion ensues in step 7, so that the sampling rate $R_{sample}$ (low) of the low-resolution portion corresponds to the sampling rate $R_{sample}$ (high) of the high-resolution portion. In step 8 a volume image V with a high-resolution portion and a low-resolution portion is generated by a filtered back-projection employing a cone beam reconstruction method.

Figure 3:
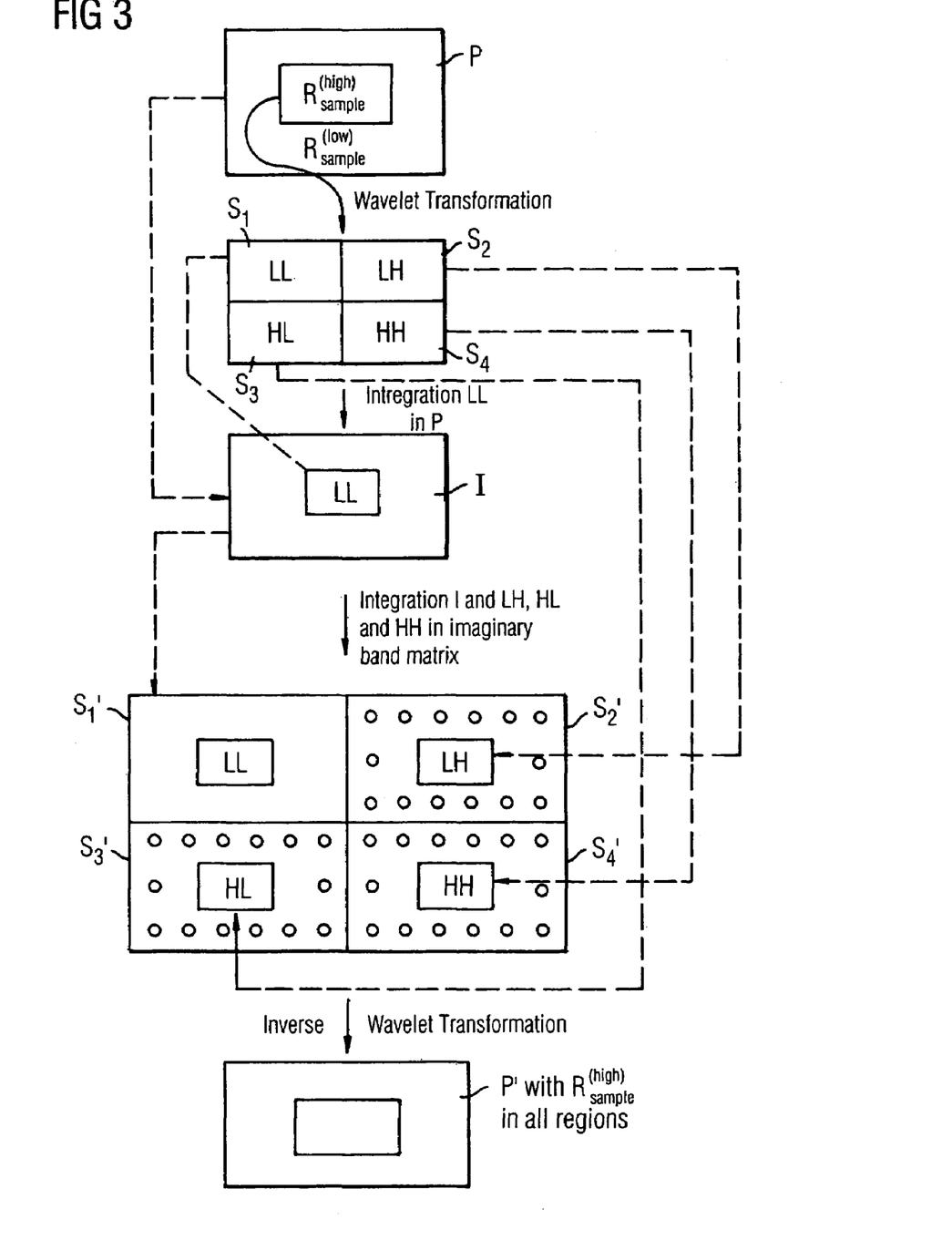
FIG. 3 is a function diagram of the inventive interpolation method.

FIG. 3 shows the sequence in the interpolation step 7 in the form of a detailed flowchart. Proceeding from a projection image P that has a middle region registered with twice as high a sampling rate $R_{sample}$ (high) and an outer region with low sampling rate $R_{sample}$ (low), which is one-half of the high sampling rate $R_{sample}$ (high) a wavelet transformation is first applied to the middle region with high sampling rate and within which four sub-bands $S_1$, $S_2$, $S_3$ and $S_4$ are generated using a low-pass filter and a high-pass filter. The sub-band $S_1$, which can be referred to as "low-low band", contains the low-pass part of the middle, high-resolution region of the projection image P in the form of approximation coefficients. The sub-bands $S_2$, $S_3$ and $S_4$, which can also be referred to as "low-high band" ($S_2$), "high-low band" ($S_3$) and "high-high band ($S_4$), contain the high-frequency parts of the middle, high-resolution region of the original projection image and were generated using the low-pass filter and the high-pass filter in the case of $S_2$ and $S_3$ and using only the high-pass filter in the case of $S_4$. The difference between the sub-bands $S_2$ and $S_3$ that the two filters employed were respectively applied in different directions.

Subsequently, the low-low sub-band $S_1$ is integrated into the original projection image at the location where the high-resolution region with the sampling rate $R_{sample}$ (high) was. An integration image I is obtained that is integrated in the following step into a further band matrix that is likewise composed of four sub-bands. The sub-bands, called sub-band $S_1'$, $S_2'$, $S_3'$ and $S_4'$, are likewise respectively low-low, low-high, high-low and high-high bands. The integration image I is now integrated into the low-low sub-band $S_1'$ of the imaginary band matrix. The three original sub-bands $S_2$, $S_3$ and $S_4$, which contain detail coefficients that indicate the high-pass part and that describe the edges and other details within the projection image I, are now respectively integrated into the corresponding sub-bands $S_2'$, $S_3'$, and $S_4'$ of the imaginary band matrix. The detail coefficients of the sub-bands $S_2$, $S_3$ and $S_4$ can be allocated to the respective pixel positions in the original projection image. These pixel positions are respectively reencountered in one of the sub-bands $S_2'$, $S_3'$, and $S_4'$ within the imaginary band matrix. The individual detail coefficients of the respective sub-bands $S_2$, $S_3$ and $S_4$ are now entered at exactly these pixel positions, which can be referred to as two-dimensional x, y-locations. They are then correspondingly located in the middle of the respective sub-bands of the imaginary band matrix. The remaining band region is filled with filler coefficients, respectively "0" here. An inverse two-dimensional wavelet transformation is now implemented. The result is a 2-D projection image, with the sampling rate being the same in all regions and corresponding to the original high sampling rate $R_{sample}$ (high). The spatial resolution, however, is twice as high in the middle region as in the outer regions. These projections images P' are subsequently processed in step 9 by means of a cone beam reconstruction method with filtered back-projection for generating the volume image V.

It should be noted that the interpolation steps up to the inverse back-projection can be multiply implemented in succession, with the number of repetitions depending on how the sampling rates between the high-resolution region and the low-resolution region differ. Each interpolation up to the inverse back-projection leads to a doubling of the sampling rate, or a doubling, of the scale.

Figure 4:
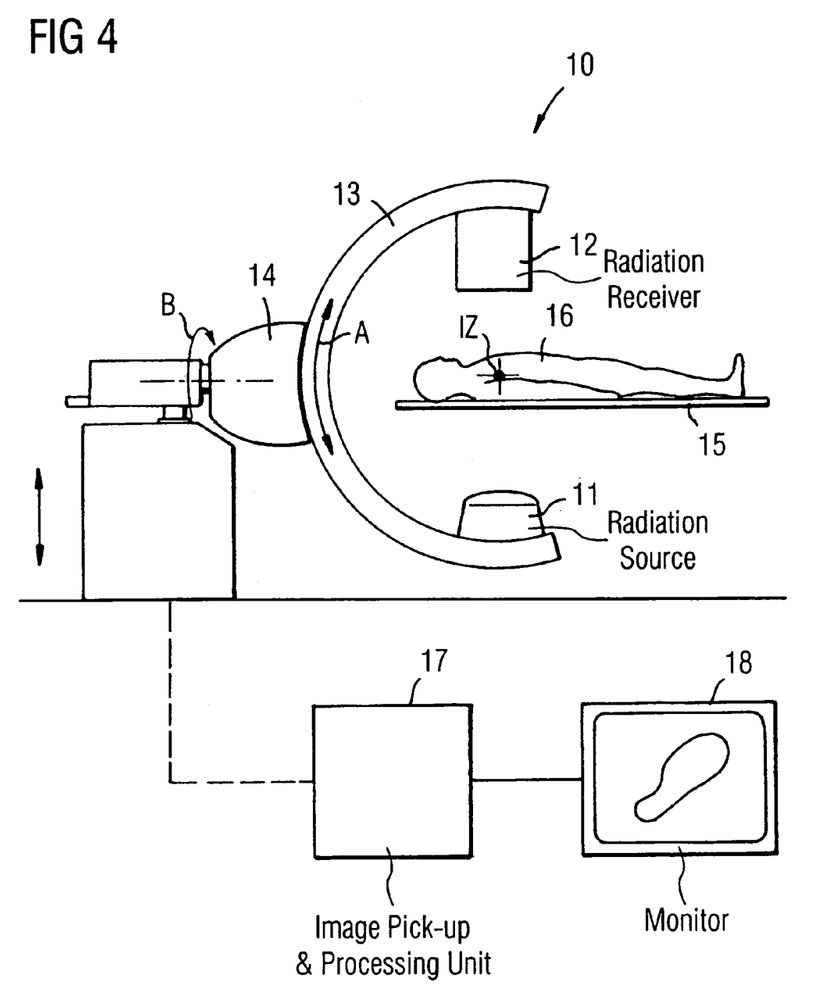
FIG. 4 is a schematic block diagram of a C-arm apparatus suitable for the implementation of the inventive method.

FIG. 4 shows an inventive apparatus 10 for the implementation of one or both embodiments of the inventive method. The apparatus 10 is in the form of a C-arm device and has a radiation source 11 and a radiation receiver 12, preferably in the form of a digital flat detector, that are both arranged at a C-arm 13 and are movable in common by the C-arm. To this end, the C-arm 13 can be moved along the arrow A in the arm mount 14. Together with the C-arm 13 and its components 11 and 12, the mount 14 is rotatable around a horizontal axis, as shown with the arrow B.

When a patient 16 lying on a patient bed 15 is to be examined, then the C-arm 13, and thus the radiation source 11 and the radiation receiver 12, is rotated around the horizontal axis along the arrow B for exposing the projection images required for the volume reconstruction. The radiation source 11 and the radiation receiver 12 thereby orbit around the patient 16. During this motion, two-dimensional projection images of the examination region, which lies in the isocenter IZ, are registered from different angles. Each individual projection image is read out from the radiation receiver 12 and is forwarded to an image pick-up and processing unit 17 where the reconstruction of one or both volume images ensues after the exposure of all projection images. All projection images required for this purpose are registered in a single scan, i.e. in a single revolution around the patient 16.

A corresponding exposure mode is required dependent on which embodiment of the image-processing method the image pick-up and processing apparatus 17 uses for the inventive volume reconstruction. Either individual projection images with different resolutions are to be registered, to which end the radiation receiver 12 is controlled via the image pick-up and processing unit 17 so that its spatial resolution is switched in alternation between high resolution and low resolution, which, for example, can ensue by means of pixel binning, if projection images with regions of different spatial resolution must be registered, a "Fovea" detector can be employed, for example, that inherently has such regions with different resolution. Alternatively, such regions can be electronically selected and switched. This also can be controlled via the image pick-up and processing unit 17.

The individual two-dimensional projection images are correspondingly processed in the image pick-up and processing unit 17 dependent on one of the embodiments of the inventive processing method. When, for example, the first embodiment is used, then a volume image with high spatial resolution is first reconstructed on the basis of the high-resolution projection images. Subsequently, the originally high-resolution projection images are transformed, so that the correspond in view of scale, sampling rate and resolution to the low-resolution projection images. From this number of images, corresponding to the total number of images "registered", which all exhibit the same scale, same sampling rate, same resolution and same plurality of pixels, a second volume image that has low spatial resolution and high contrast resolution is then reconstructed. The reconstructed images are subsequently presented at a monitor 18 either individually or in common (possibly overlaid).

When projection images that have different resolution by regions are registered, an interpolation of the data of the low-resolution region is implemented in the image pick-up and processing unit 17 for the adaptation of the sampling rate of the low-resolution region to that of the high-resolution region. Subsequently, the volume image is reconstructed by means of a cone beam volume reconstruction method with filtered back-projection of the projection images having a uniform sampling rate. This volume image then exhibits a high-resolution region, for example in the middle of the volume, and a low-resolution region, for example at the edge. This volume image multiply resolved in regions is presented at the monitor 18 for evaluation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating three-dimensional, multiply resolved volume images of an examination subject, comprising the steps of:
    in an exposure procedure, irradiating an examination subject with X-rays from a radiation source and detecting X-rays attenuated by the subject with a radiation receiver and thereby registering a plurality of low-resolution two-dimensional projection images and a plurality of high-resolution two-dimensional projection images, said low resolution projection images and said high-resolution projection images each having a scale and a sampling rate associated therewith;
    transforming said high-resolution projection images, and still retaining said high-resolution projection images, to produce transformed projection images having a scale and a sampling rate which are the same as the scale and the sampling rate of said low-resolution projection images; and
    generating a three-dimensional volume image having a low resolution from said low-resolution projection images and said transformed projection images, and generating a three-dimensional volume image with high resolution from said high-resolution projection images.

2. A method as claimed in claim 1 wherein said radiation detector contains a plurality of pixels, and comprising generating said low-resolution projection images by interconnecting selected juxtaposed pixels in said plurality of pixels.

3. A method as claimed in claim 1 comprising registering said low-resolution projection images and said high-resolution projection images in a predetermined, alternating sequence.

4. A method as claimed in claim 3 comprising registering a total of N projection images, with every $n^{th}$ projection image being registered with high resolution.

5. A method as claimed in claim 1 comprising reconstructing the respective three-dimensional volume images using a conical beam reconstruction method.

6. A method as claimed in claim 5 comprising reconstructing the respective three-dimensional volume images in a conical beam reconstruction method with filtered back-projection.

7. A method as claimed in claim 6 comprising employing a filter which promotes contrast resolution in the filtered back-projection for generating said three-dimensional volume image with low resolution.

8. A method as claimed in claim 6 comprising employing a filter which promotes spatial resolution in said filtered back-projection.

9. A method as claimed in claim 1 comprising the additional step of presenting said respective three-dimensional volume images on a display monitor in a presentation mode selected from the group consisting of individual presentation of the respective three-dimensional volume images and overlaid presentation of the three-dimensional volume images.

10. A method for generating three-dimensional, multiply resolved volume images of an examination subject, comprising the steps of:
in an examination procedure, irradiating an examination subject with x-rays from a radiation source and detecting x-rays attenuated by said subject with a radiation detector having a high-resolution detection region and a low-resolution detection region, and thereby obtaining a plurality of two-dimensional projection images each having a high resolution portion obtained from said high-resolution region of said radiation receiver and a low-resolution portion obtained from said low-resolution region of said radiation receiver, and in each of said projection images, said high-resolution portion and said low-resolution portion each having a sampling rate associated therewith;
interpolating the low-resolution portion of each projection image to adapt the sampling rate thereof so that the sampling rate of said low-resolution portion is equal to the sampling rate of the high-resolution portion; and
executing a filtered back-projection of said plurality of projection images with a uniform sampling rate and thereby generating a three-dimensional volume image having a volume portion with high resolution and a volume portion with low resolution.

11. A method as claimed in claim 10 wherein said radiation receiver contains a plurality of pixels and comprising obtaining the respective low-resolution portions of said projection images by interconnecting selected juxtaposed pixels in said low-resolution region of said radiation detector.

12. A method as claimed in claim 10 wherein the step of interpolating the low-resolution portion in each of said projection images comprises:
filtering the high-resolution portion of said projection image separately with a low-pass filter and a high-pass filter in a two-dimensional wavelet transformation, thereby obtaining a band matrix containing four sub-bands, one of said sub-bands containing only a low-pass filtered portion of the projection image comprised of approximation coefficients, and the others of said sub-bands respectively containing different high-pass portions of said projection image comprising detail coefficients;
integrating the sub-band comprising approximation coefficients in each of said projection images, instead of integrating the high-resolution portion of that projection image, to obtain an integration image with a lower resolution;
employing said integration image as a low-pass sub-band in a second band matrix, also having a total of four sub-bands;
filling the other sub-bands of said second band matrix with said detailed coefficients of said sub-bands of said first band matrix at positions in said second band matrix respectively corresponding with positions in said first band matrix, and with filler coefficients at all other positions in said second band matrix; and
subjecting said second band matrix to an inverse wavelet transformation.

13. A method as claimed in claim 12 wherein the step of filling all other positions in said second band matrix with filler coefficients comprises filling all other positions in said second band matrix with filler coefficients having a value of zero.

14. A method as claimed in claim 12 comprising repeating the steps of filtering said high-resolution region, integrating said sub-band, employing said integration image as a low-pass sub-band, filling said second band matrix, and subjecting said second band matrix to an inverse wavelet transformation, until said sampling rate of said low-resolution portion equals the sampling rate of said high-resolution portion.

15. A method as claimed in claim 10 comprising employing a radiation detector having a variable high-resolution region as said radiation detector.

16. An apparatus for generating three-dimensional, multiply resolved volume images of an examination subject, comprising:
an x-ray source and a radiation receiver for, in an exposure procedure, irradiating an examination subject with X-rays from said radiation source and detecting X-rays attenuated by the subject with said radiation receiver and thereby registering a plurality of low-resolution two-dimensional projection images and a plurality of high-resolution two-dimensional projection images, said low resolution projection images and said high-resolution projection images each having a scale and a sampling rate associated therewith;
an image-processing unit for transforming said high-resolution projection images, and still retaining said high-resolution projection images, to produce transformed projection images having a scale and a sampling rate which are the same as the scale and the sampling rate of said low-resolution projection images; and
said image-processing unit generating a three-dimensional volume image having a low resolution from said low-resolution projection images and said transformed projection images, and generating a three-dimensional volume image with high resolution from said high-resolution projection images.

17. An apparatus for generating three-dimensional, multiply resolved volume images of an examination subject, comprising the steps of:

an x-ray source and a radiation receiver having a high-resolution detection region and a low-resolution detection region for, in an examination procedure, irradiating an examination subject with x-rays from said radiation source and detecting x-rays attenuated by said subject with said radiation detector, and thereby obtaining a plurality of two-dimensional projection images each having a high resolution portion obtained from said high-resolution region of said radiation receiver and a low-resolution portion obtained from said low-resolution region of said radiation receiver, and in each of said projection images, said high-resolution portion and said low-resolution portion each having a sampling rate associated therewith;

an image-processing unit for interpolating the low-resolution portion of each projection image to adapt the sampling rate thereof so that the sampling rate of said low-resolution portion is equal to the sampling rate of the high-resolution portion; and said image-processing unit executing a filtered back-projection of said plurality of projection images with a uniform sampling rate and thereby generating a three-dimensional volume image having a volume portion with high resolution and a volume portion with low resolution.

* * * * *